United States Patent
Kim et al.

(10) Patent No.: US 11,015,197 B2
(45) Date of Patent: May 25, 2021

(54) THERAPEUTIC AGENT FOR TREATING CANCER COMPRISING ANTI-MIRNA-ALBUMIN COMPOSITE

(71) Applicant: KOREA INSTITUTE OF SCIENCE AND TECHNOLOGY, Seoul (KR)

(72) Inventors: Sun Hwa Kim, Seoul (KR); Ick Chan Kwon, Seoul (KR); Kwangmeyung Kim, Seoul (KR); Hong Yeol Yoon, Seoul (KR); Gi-Jung Kwak, Seoul (KR); Juho Park, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/425,849

(22) Filed: May 29, 2019

(65) Prior Publication Data
US 2020/0071698 A1    Mar. 5, 2020

(30) Foreign Application Priority Data
Aug. 29, 2018   (KR) .......... 10-2018-0102103

(51) Int. Cl.
*C12N 15/113*   (2010.01)
*A61P 35/00*   (2006.01)

(52) U.S. Cl.
CPC ........... *C12N 15/113* (2013.01); *A61P 35/00* (2018.01); *C12N 2310/315* (2013.01); *C12N 2310/3231* (2013.01); *C12N 2310/351* (2013.01); *C12N 2310/3513* (2013.01); *C12N 2320/52* (2013.01); *C12N 2320/53* (2013.01)

(58) Field of Classification Search
CPC ......... C12N 15/113; C12N 2310/3513; C12N 2310/3231; C12N 2320/52; C12N 2320/53; C12N 2310/315; C12N 2310/351; C12N 2310/113; A61P 35/00
See application file for complete search history.

(56) References Cited

U.S. PATENT DOCUMENTS

2009/0203893 A1*   8/2009   Esau ............... C12N 15/111
                                              536/24.5

FOREIGN PATENT DOCUMENTS

KR   10-2012-0047892 A   5/2012

OTHER PUBLICATIONS

Lau et al. (Mol Pharm 2012, 9, pp. 71-80) (Year: 2012).*
Don Rio, RNA 2018, "The 23$^{rd}$ Annual Meeting of the RNA Society", University of California, Berkeley, No. 693, May 29-Jun. 3, 2018, total of 520 pages.
Costa et al., "Tumor-targeted Chlorotoxin-coupled Nanoparticles for Nucleic Acid-Delivery to Glioblastoma Cells: A Promising System for Glioblastoma Treatment," Molecular Therapy—Nucleic Acids (2013), vol. 2, e100, pp. 1-13.
Ming et al., "Albumin-based Nanoconjugates for Targeted Delivery of Therapeutic Oligonucleotides." Biomaterials (Oct. 2013), vol. 34. No. 32, pp. 1-22.

* cited by examiner

*Primary Examiner* — J. E. Angell
(74) *Attorney, Agent, or Firm* — Birch, Stewart, Kolasch & Birch, LLP

(57) ABSTRACT

The present invention relates to a novel anti-miRNA single-stranded nucleic acid maleimide derivative, which comprises an anti-miRNA single-stranded nucleic acid having a nucleic acid sequence complementary to a nucleic acid sequence of an miRNA. Further, the present invention provides an anti-miRNA single-stranded nucleic acid-serum albumin conjugate in which serum albumin is covalently bonded to the anti-miRNA single-stranded nucleic acid maleimide derivative via the maleimide group.

18 Claims, 13 Drawing Sheets
Specification includes a Sequence Listing.

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: anti-21-AM

<400> SEQUENCE: 1
tcaacatcag tctgataagc ta                                              22
```

<210> SEQ ID NO 2
<211> LENGTH: 22
<212> TYPE: DNA
<213> ORGANISM: Artificial Sequence
<220> FEATURE:
<223> OTHER INFORMATION: anti-21-AM(backbone modified)
<220> FEATURE:
<221> NAME/KEY: variation
<222> LOCATION: (1)..(6)
<223> OTHER INFORMATION: phosphorothioate nucleic acid
<220> FEATURE:
<221> NAME/KEY: variation
<222> LOCATION: (17)..(22)
<223> OTHER INFORMATION: phosphorothioate nucleic acid
<220> FEATURE:
<221> NAME/KEY: variation
<222> LOCATION: (2)
<223> OTHER INFORMATION: locked nucleic acid
<220> FEATURE:
<221> NAME/KEY: variation
<222> LOCATION: (5)
<223> OTHER INFORMATION: locked nucleic acid
<220> FEATURE:
<221> NAME/KEY: variation
<222> LOCATION: (8)
<223> OTHER INFORMATION: locked nucleic acid
<220> FEATURE:
<221> NAME/KEY: variation
<222> LOCATION: (11)
<223> OTHER INFORMATION: locked nucleic acid
<220> FEATURE:
<221> NAME/KEY: variation
<222> LOCATION: (14)
<223> OTHER INFORMATION: locked nucleic acid
<220> FEATURE:
<221> NAME/KEY: variation
<222> LOCATION: (17)
<223> OTHER INFORMATION: locked nucleic acid
<220> FEATURE:
<221> NAME/KEY: variation
<222> LOCATION: (20)
<223> OTHER INFORMATION: locked nucleic acid

<400> SEQUENCE: 2
tcaacatcag tctgataagc ta                                              22

<210> SEQ ID NO 3
<211> LENGTH: 22
<212> TYPE: DNA
<213> ORGANISM: Artificial Sequence
<220> FEATURE:
<223> OTHER INFORMATION: anti-neg-AM

<400> SEQUENCE: 3
gcgtattata gccgattaac ga                                              22

<210> SEQ ID NO 4
<211> LENGTH: 22
<212> TYPE: DNA
<213> ORGANISM: Artificial Sequence
<220> FEATURE:
<223> OTHER INFORMATION: anti-neg-AM(backbone modified)
<220> FEATURE:
<221> NAME/KEY: variation
<222> LOCATION: (1)..(6)
<223> OTHER INFORMATION: phosphorothioate nucleic acid
<220> FEATURE:
<221> NAME/KEY: variation
<222> LOCATION: (17)..(22)
<223> OTHER INFORMATION: phosphorothioate nucleic acid
<220> FEATURE:
<221> NAME/KEY: variation
<222> LOCATION: (2)

```
<223> OTHER INFORMATION: locked nucleic acid
<220> FEATURE:
<221> NAME/KEY: variation
<222> LOCATION: (5)
<223> OTHER INFORMATION: locked nucleic acid
<220> FEATURE:
<221> NAME/KEY: variation
<222> LOCATION: (8)
<223> OTHER INFORMATION: locked nucleic acid
<220> FEATURE:
<221> NAME/KEY: variation
<222> LOCATION: (11)
<223> OTHER INFORMATION: locked nucleic acid
<220> FEATURE:
<221> NAME/KEY: variation
<222> LOCATION: (14)
<223> OTHER INFORMATION: locked nucleic acid
<220> FEATURE:
<221> NAME/KEY: variation
<222> LOCATION: (17)
<223> OTHER INFORMATION: locked nucleic acid
<220> FEATURE:
<221> NAME/KEY: variation
<222> LOCATION: (20)
<223> OTHER INFORMATION: locked nucleic acid

<400> SEQUENCE: 4
gcgtattata gccgattaac ga                                          22
```

THERAPEUTIC AGENT FOR TREATING CANCER COMPRISING ANTI-MIRNA-ALBUMIN COMPOSITE

CROSS-REFERENCES TO RELATED APPLICATIONS

This application claims the benefit of and priority to Korean Patent Application No. 10-2018-0102103, filed on Aug. 29, 2018, which is incorporated herein by this reference in its entirety.

TECHNICAL FIELD

The present invention relates to a cancer therapeutic agent comprising a complex of miRNA inhibitor-albumin as an active ingredient, and more particularly, to a cancer therapeutic agent comprising a complex of miRNA inhibitor-albumin with an improved half-life in vivo as an active ingredient.

BACKGROUND OF THE INVENTION

MicroRNAs (miRNAs) are single-stranded oligomers consisting of 20 to 24 nucleotides that modulate transiently specific gene expression according to the nucleic acid sequence structure, affecting intracellular signal pathways such as apoptosis, differentiation, division, and metabolism thereby and relate to various diseases such as cancer, infection, immune disease. In addition, miRNA inhibitors such as anti-miRNA (antagonist miRNA or blockmir) and miRNA sponge, which are single stranded antisense oligonucleotides (ASOs), have been used to study and treat diseases caused by miRNAs. However, there are problems such as in vivo instability of miRNA inhibitor and low targeting ability to affected sites and thus various carriers which are chemically modified nucleotides, liposomes, polymer and protein complex such as phosphorothioates, neutral backbones (phosphorodiamidate morpholino oligomer, PMO), peptide nucleic acid (PNA), 2'-O-methylated oligonucleotides (2'-O-Me), 2'-O-methoxyethylated oligonucleotides (2'-O-MOE), bridged rings (LNA) have been applied. Nevertheless, carrier-free miRNA inhibitors are injected in large amounts for drug efficacy due to rapid release in vivo and low targeting ability to affected sites, resulting in adverse effects in normal tissues and even though carriers are used the potential risk and complexity of carriers make it difficult to commercialize. In this regard, Korean Patent Publication No. 2012-0047892 discloses a chemical modified motif for miRNA inhibitors and analogs thereof.

SUMMARY OF THE INVENTION

However, the prior art has problems such as in vivo instability of miRNA inhibitors and side effects due to low targeting ability to affected sites.

The present invention has been made to overcome the above-mentioned problems, and it is an object of the present invention to provide a pharmaceutical composition comprising a miRNA inhibitor-albumin complex, which exhibits high in vivo stability by being circulated in a long time and delivered to affected sites effectively as an active ingredient. However, these problems are exemplary and do not limit the scope of the present invention.

In an aspect of the present invention, there is provided an anti-miRNA single-stranded nucleic acid maleimide derivative to which a maleimide group is added at either end of an anti-miRNA single-stranded nucleic acid molecule having a nucleic acid sequence complementary to a miRNA.

In another aspect of the present invention, there is provided an anti-miRNA single-stranded nucleic acid-serum albumin conjugate in which a serum albumin is covalently bound to the anti-miRNA single-stranded nucleic acid maleimide derivative via the maleimide group.

In another aspect of the present invention, there is provided a composition for inhibiting miRNA comprising the anti-miRNA single-stranded nucleic acid maleimide derivative as an active ingredient.

In another aspect of the present invention, there is provided a composition for inhibiting miRNA comprising the anti-miRNA single-stranded nucleic acid-serum albumin conjugate as an active ingredient.

In another aspect of the present invention, there is provided a composition for treating cancer comprising an anti-miR-21 single-stranded nucleic acid maleimide derivative in which a maleimide group is added to either end of an anti-miR-21 single-stranded nucleic acid having a nucleic acid sequence complementary to a miR-21.

In another aspect of the present invention, there is provided a method of inhibiting a miRNA in a subject in need of comprising administering therapeutically effective amount of the anti-miRNA single-stranded nucleic acid maleimide derivative to the subject.

In another aspect of the present invention, there is provided a method of inhibiting a miRNA in a subject in need of, wherein the method comprise administering therapeutically effective amount of the anti-miRNA single-stranded nucleic acid-serum albumin conjugate to the subject.

In another aspect of the present invention, there is provided a method of stabilizing an anti-miRNA single-stranded nucleic acid in a subject in need of, wherein the method comprises preparing said anti-miRNA single-stranded nucleic acid maleimide derivative to which a maleimide group is added at either end of an anti-miRNA single-stranded nucleic acid having a nucleic acid sequence complementary to a miRNA; and administering therapeutically effective amount of the anti-miRNA single-stranded nucleic acid maleimide derivative to the subject.

In another aspect of the present invention, there is provided a method of stabilizing an anti-miRNA single-stranded nucleic acid in a subject in need of, wherein the method comprises preparing said anti-miRNA single-stranded nucleic acid-serum albumin conjugate in which a serum albumin is covalently bound to the anti-miRNA single-stranded nucleic acid maleimide derivative via the maleimide group; and administering therapeutically effective amount of the anti-miRNA single-stranded nucleic acid-albumin conjugate to the subject.

In another aspect of the present invention, there is provided a method for treating cancer in a subject, the method comprising administering an anti-miR-21 single-stranded nucleic acid maleimide derivative in which a maleimide group is added to either end of an anti-miR-21 single-stranded nucleic acid having a nucleic acid sequence complementary to a miR-21 to the subject.

In another aspect of the present invention, there is provided a method for treating cancer in a subject, the method comprising administering an anti-miR-21 single-stranded nucleic acid-albumin conjugate in which a serum albumin is covalently bound to an anti-miR-21 single-stranded nucleic acid maleimide derivative in which a maleimide group is added to either end of an anti-miR-21 single-stranded nucleic acid having a nucleic acid sequence complementary to a miR-21 via the maleimide group to the subject.

Effects of the Invention

As described above, according to one embodiment of the present invention, the use of the miRNA inhibitor-albumin complex of the present invention improves the low in vivo stability and low targeting ability to affected sites which were problems of conventional miRNA inhibitors. Of course, the scope of the present invention is not limited by these effects.

DETAILED DESCRIPTION OF THE INVENTION

Definitions

Figure 1A:
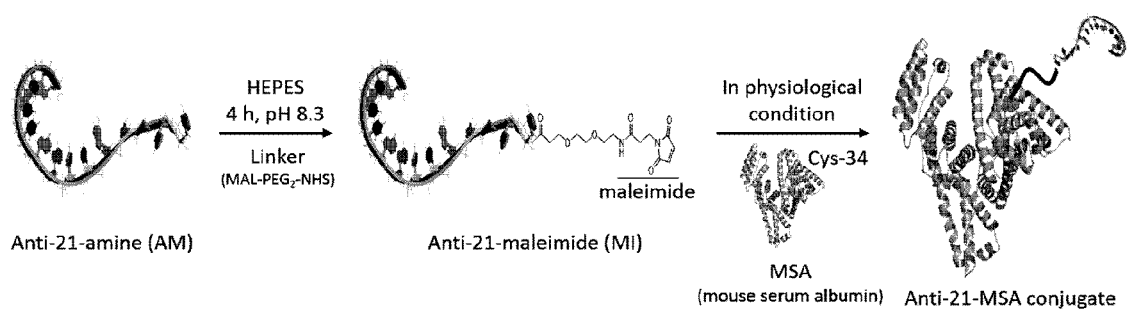
FIG. 1A is a schematic diagram illustrating the synthesis of miRNA inhibitors and the reaction with albumin.

As used herein, the term "microRNA (miRNA)" is a small RNA that controls the gene expression of an organism.

Usually mRNA is made up of several thousand nucleotides, whereas microRNA is composed of 20 to 25 nucleotides.

As used herein, "albumin" is a simple protein widely distributed in living cells or body fluids and constitutes the basic material of cells together with globulin, and is widely present in the tissues of plants and animals. Animal albumin includes egg albumin, serum albumin, lacto-albumin in milk, albumin in liver and muscle, and vegetable albumin includes leukosin (barley), regumelin (pea), and ricin (castor).

DETAILED DESCRIPTION OF THE INVENTION

In an aspect of the present invention, there is provided an anti-miRNA single-stranded nucleic acid maleimide derivative to which a maleimide group is added at either end of an anti-miRNA single-stranded nucleic acid molecule having a nucleic acid sequence complementary to a miRNA.

According to anti-miRNA single-stranded nucleic acid maleimide derivative, the miRNA may be selected from the group consisting of miR-21, miR-17, miR-18, miR-19, miR-20, miR-21, miR-22, miR-23, miR-24, miR-25, miR-26, miR-27, miR-29, miR-30, miR-31, miR-32, miR-33, miR-34, miR-35, miR-36, miR-37, miR-38, miR-39, miR-40m, miR-41, miR-42, miR-43, miR-44, miR-45, miR-46, miR-47, miR-48, miR-49, miR-50, miR-51, miR-52, miR-53, miR-54, miR-55, miR-56, miR-57, miR-58, miR-59, miR-60, miR-61, miR-66, miR-67, miR-68, miR-69, miR-70, miR-71, miR-72, miR-73, miR-74, miR-75, miR-76, miR-77, miR-78, miR-79, miR-80, miR-81, miR-82, miR-83, miR-84, miR-85, miR-86, miR-87, miR-88, miR-89, miR-90, miR-91, miR-92, miR-324a, miR-205, miR-182, miR-133b, miR-206, miR-193a-3p, miR-129-5p, miR-144-5p, miR-19a, miR-211, miR-185, miR-133b, miR-205, miR-373, miR-155, miR-31-3p, miR-194, miR-143, miR-449a, miR-224, miR-21, miR-483-3p, miR-221, miR-122, miR-612, miR-152-5p, miR-22, miR-145, miR-125a, miR-126, miR-21, miR-181d, miR-10b, miR-589-3p, miR-194-5p, miR-26a, miR-182, miR-145, miR-29b, miR-138, miR-21, miR-494, miR-1973, miR-21, miR-96, miR-200a, miR-200b, miR-200c, miR-141, miR-429, miR-205, miR-212, miR-342, miR-214, miR-424, miR-503, miR-17-5p, miR-196a, miR-21, miR-1246, miR-196a, miR-196b, miR-506, miR-214, miR-383, miR-34a, miR-744-5p, miR-7, miR-21-3p, miR-199a, miR-214, miR-200c, miR-888, miR-892c, miR-890, miR-892a, miR-892b, miR-891b, miR-891a, miR-214, miR-219-5p, miR-493, miR-4286, miR-378a-3p, miR-23a, miR-146a, miR-339-3p, miR-216b, miR-186, miR-21, miR-210, miR-421, miR-373, miR-155, miR-181d, miR-15, miR-16, miR-26a, miR-196a2, Let-7a, miR-182, miR-504, miR-125b, miR-100, miR-18a, miR-101, miR-34c, miR-185, miR-125b, miR-18a, miR-192, miR-182, miR-373, miR-712, miR-205, miR-17-92, miR-1, miR-222, miR-223, miR-146a, miR-221, miR-130a, miR-155, miR-376, miR-208a, miR-15b, miR-18a, miR-19b, miR-21, miR-24, miR-30c, miR-92a miR-106a, miR-125b-5p, miR-130a, miR-145, miR-152, miR-181a, miR-214, miR-222, miR-296-5p, miR-302a, miR-307, miR-381, miR-124, miR-132, miR-134, miR-138, miR-155, miR-23a, miR-129, miR-133a, miR-155, miR-221, miR-222, Let-7, miR-383, miR-146a, miR-146b, miR-33, miR-519d, miR-374a-5p, miR-26b, miR-27a, miR-21, miR-34a, miR-101-3p, miR-122, miR-130a, miR-137, miR-146a-5p, miR-181a, miR-373, miR-204, miR-1236, miR-143, miR-145, miR-5193, miR-93-5p and miR-602.

According to anti-miRNA single-stranded nucleic acid maleimide derivative, the anti-miRNA single-stranded nucleic acid molecule may be one whose skeleton is partially or wholly modified, and the anti-miRNA single-stranded nucleic acid whose skeleton is modified may be PS (phosphorothioate) modified nucleic acid, PNA (peptide nucleic acid), PMO (phosphorodiamidate morpholino oligomer) or 2'-modified nucleic acid, and the 2'-modified nucleic acid may be 2'-O-methyl (2'-O-methyl) modified nucleic acid, or a 2'-O-methoxyethyl (2'-O-MOE) modified nucleic acid.

According to anti-miRNA single-stranded nucleic acid maleimide derivative, the skeleton may be modified at a ratio of one of three consecutive nucleotide.

In another aspect of the present invention, there is provided an anti-miRNA single-stranded nucleic acid-serum albumin conjugate in which a serum albumin is covalently bound to the anti-miRNA single-stranded nucleic acid maleimide derivative via the maleimide group.

According to another aspect of the present invention, there is provided a composition for inhibiting miRNA comprising the anti-miRNA single-stranded nucleic acid molecule maleimide derivative as an active ingredient.

According to another aspect of the present invention, there is provided a composition for inhibiting miRNA comprising the anti-miRNA single-stranded nucleic acid-serum albumin conjugate as an active ingredient.

According to the composition for inhibiting miRNA, it can be used for the treatment of a disease caused by the over-expression of the miRNA, and can be used for a reagent for studying the biological function of the miRNA.

In another aspect of the present invention, there is provided a composition for treating cancer comprising an anti-miR-21 single-stranded nucleic acid maleimide derivative in which a maleimide group is added to either end of an anti-miRNA single-stranded nucleic acid having a nucleic acid sequence complementary to a miRNA.

In another aspect of the present invention, there is provided a method of inhibiting a miRNA in a subject in need of comprising administering therapeutically effective amount of the anti-miRNA single-stranded nucleic acid maleimide derivative to the subject.

In another aspect of the present invention, there is provided a method of inhibiting a miRNA in a subject in need of, wherein the method comprise administering therapeutically effective amount of the anti-miRNA single-stranded nucleic acid-serum albumin conjugate to the subject.

In another aspect of the present invention, there is provided a method of stabilizing an anti-miRNA single-stranded nucleic acid in a subject in need of, wherein the method comprises preparing said anti-miRNA single-stranded nucleic acid maleimide derivative to which a maleimide group is added at either end of an anti-miRNA single-stranded nucleic acid having a nucleic acid sequence complementary to a miRNA; and administering therapeutically effective amount of the anti-miRNA single-stranded nucleic acid maleimide derivative to the subject.

In another aspect of the present invention, there is provided a method of stabilizing an anti-miRNA single-stranded nucleic acid in a subject in need of, wherein the method comprises preparing said anti-miRNA single-stranded nucleic acid-serum albumin conjugate in which a serum albumin is covalently bound to the anti-miRNA single-stranded nucleic acid maleimide derivative via the maleimide group; and administering therapeutically effective amount of the anti-miRNA single-stranded nucleic acid-albumin conjugate to the subject.

In another aspect of the present invention, there is provided a method for treating cancer in a subject, the method comprising administering an anti-miR-21 single-stranded nucleic acid maleimide derivative in which a maleimide group is added to either end of an anti-miR-21 single-stranded nucleic acid having a nucleic acid sequence complementary to a miR-21 to the subject.

In another aspect of the present invention, there is provided a method for treating cancer in a subject, the method comprising administering an anti-miR-21 single-stranded nucleic acid-albumin conjugate in which a serum albumin is covalently bound to an anti-miR-21 single-stranded nucleic acid maleimide derivative in which a maleimide group is added to either end of an anti-miR-21 single-stranded nucleic acid having a nucleic acid sequence complementary to a miR-21 via the maleimide group to the subject.

The term "therapeutically effective amount" as used herein refers to an amount sufficient to treat a disease at a reasonable benefit/risk ratio applicable to medical treatment, and the effective dose level will depend on the type of subject and severity of the symptom, age, sex, sensitivity to the drug, time of administration, route of administration, rate of excretion, duration of treatment, factors including co-administered drugs, and other factors well known in the medical field. The amount to be used is not particularly limited, but may be 0.01 µg/kg/day to 10 mg/kg/day. The above-mentioned daily dose may be administered once a day or twice or three times a day at appropriate intervals, or intermittently administered at intervals of several days.

The pharmaceutical composition of the present invention may further contain suitable carriers, excipients and diluents which may be contained in an amount of 0.1 to 100% by weight based on the total weight of the composition and are conventionally used in the production of a pharmaceutical composition. In addition, solid pharmaceutical preparations or liquid pharmaceutical preparations can be used for the preparation of pharmaceutical compositions. The preparation additive may be either organic or inorganic. Examples of excipients include lactose, sucrose, saccharose, glucose, cornstarch, starch, talc, sorbit, crystalline cellulose, dextrin, kaolin, calcium carbonate and silicon dioxide. Examples of the binder include polyvinyl alcohol, polyvinyl ether, ethylcellulose, methylcellulose, gum arabic, tragacanth, gelatin, shellac, hydroxypropylcellulose, hydroxypropylmethylcellulose, calcium citrate, Dextrin and pectin, and the like. Examples of the lubricant include magnesium stearate, talc, polyethylene glycol, silica, and hydrogenated vegetable oil. Any coloring agent may be used as long as it is usually allowed to be added to pharmaceuticals. These tablets and granules can be suitably coated with sugar (sugar coating), gelatin coating, and others as required. If necessary, preservatives, antioxidants and the like may be added.

The pharmaceutical composition of the present invention can be prepared by any of the formulations conventionally produced in the art (for example, Remington's Pharmaceutical Science (latest edition; Mack Publishing Company, Easton Pa.), the form of the formulation is not particularly limited. These formulations are described in Remington's Pharmaceutical Science, 15th Edition, 1975, Mack Publishing Company, Easton, Pa. 18042 (Chapter 87: Blaug, Seymour), a formulation generally known in all pharmaceutical chemistries.

The pharmaceutical composition of the present invention can be administered orally or parenterally. Preferably, parenteral administration is performed by intravenous injection, subcutaneous injection, intracerebroventricular injection, intracerebrospinal fluid injection, intramuscular injection and intraperitoneal injection.

Carrier-free miRNA inhibitors under the research and development in order to improve the in vivo instability of inhibitors of miRNA deeply related to various diseases such as cancer, infectious diseases, immune diseases and the like, should be administered to a subject in a large amount due to rapid clearance in vivo and low targeting ability to affected sites, which was causing concern about side effects to normal tissues. In addition, even if a carrier is used, it has been difficult to commercialize the carrier due to the potential danger and complexity of the carrier. Therefore, the present inventors have made efforts to develop a novel miRNA inhibitor having improved in vivo stability, which is circulated for a long time in a form retaining in vivo activity and is effectively delivered to affected sites in order to overcome the above-mentioned problems. As a result, the present inventors completed the present invention by specifying miRNA-21, one of oncogenes as a target miRNA, and synthesizing a maleimide derivative of an anti-miR21 inhibitor (Anti-21-MI) by adding malemide-PEG2-NHS ester linker to an amine-modified miR-21 inhibitor (anti-21-AM) and confirming the maleimide derivative of an anti-miR-21 inhibitor is bio-converted to a miR-21 inhibitor-albumin conjugate (anti-21-MSA) having long in vivo lifetime when administered in vivo, succeeding to develop a new concept of anti-miRNA compound.

One of conventional nucleotide-base gene expression inhibitors is a siRNA-albumin conjugate which targeted to the heart, but the pharmacological efficiency of the siRNA-albumin conjugate can be greatly inhibited because various mediating proteins (RISC and Ago) are necessary for the action mechanism of siRNA. However, it was confirmed experimentally that the maleimide-modified anti-miRNA single-stranded nucleic acid according to an embodiment of the present invention covalently bonds in situ with the serum albumin in the plasma of a subject and forms a complex with the serum albumin when administered in vivo. In the case of miRNA inhibitors, the target miRNA is silenced through simple sequence-specific hybridization. Therefore, unlike siRNA, the formation of the miRNA inhibitor-albumin complex does not inhibit pharmacological effects, and is capable of targeting caner and inflammatory condition which are disease whose energy metabolism is abnormally fast or the blood vessels of affected site are swollen effectively. Therefore, the maleimide-modified anti-miRNA single-stranded nucleic acid according to an embodiment of the present invention can be a highly efficient miRNA targeting drug having high in vivo stability without a separate drug delivery vehicle.

BEST MODE FOR THE INVENTION

Hereinafter, the present invention will be described in more detail by following examples and experimental examples. It will be apparent to those skilled in the art that the present invention is not limited to the disclosed examples, but may be embodied in many different forms and the examples are provided in order to complete the disclosure of the present invention and to fully convey the scope of the invention to those skilled in the art.

Example 1: Materials

All nucleoside phosphoramidite monomers and trichloroacetic acid, tetrazole, iodine, acetic anhydride and N-methylimidazole which are reagents for the synthetic processes (deblocking, coupling, oxidation, and capping) were purchased from Sigma-Aldrich (St. Louis, Mo., USA).

Example 2: Synthesis of miR-21 Inhibitor (Anti-21-MI)

The present inventors selected miR-21 which is one of oncogenes as a targeted mRNA in order to solve the problems of conventional miRNA inhibitors and synthesized a maleimide-modified miR-21 inhibitor (anti-21-MI). Specifically, the present inventors started synthesis of the miR-21 inhibitor from the nucleotide-attached solid support and synthesized according to the nucleotide sequence, cycling the processes of deblocking, coupling, oxidation, and capping for each nucleic acid and coupled an amine group to 3'-end of the synthesized miR-21 inhibitors. The present inventors synthesized anti-21-AM having a nucleotide sequence of 5'-TCA ACA TCA GTC TGA TAA GCT A-3'-amine (SEQ ID NO: 1) which is a complementary sequence of mature miR-21 and anti-21-AM (backbone modifications) having a nucleotide sequence of 5'-TCA ACA TCA GTC TGA TAA GCT A-3'-amine (SEQ ID NO: 2). The molecular weight of synthesized anti-miR-21 inhibitors was confirmed by reverse-phase HPLC and MALD-TOF analysis.

Also for the maleimide modification, the amine group of the anti-21-AM was reacted with the NHS ester group of 10-fold molar ratio of the maleimide-PEG2-NHS ester linker in 0.1 M 4-(2-hydroxyethyl)-1-piperazineethanesulfonic acid (HEPES) buffer for 4 hours at room temperature. The malemide-PEG2-NHS ester linker was conjugated to an amine-modified miRNA-21 inhibitor (anti-21-AM) to synthesize a maleimide-modified miRNA-21 inhibitor (anti-21-MI). Negative controls (anti-neg-AM and anti-neg-AM (backbone modified) were synthesized in order to verify the efficiency of the miR-21 inhibitors synthesized. The maleimide-modified miRNA inhibitors were purified twice using a NAP-5 column (GE Healthcare Life Sciences, Pittsburgh, Pa., USA) and lyophilized. The purified maleimide-modified miRNA inhibitors were quantified using Biophotometer plus (Eppendorf, Hamburg, Germany). The nucleotide sequence information of the miRNA inhibitors synthesized in the present invention is summarized in the following Table 1.

TABLE 1

Nucleotide sequence information of miRNA inhibitors

| Names of miR-21 inhibitors | Nucleotide sequence (5'-->3') | SEQ ID NO |
|---|---|---|
| anti-21-AM | TCA ACA TCA GTC TGA TAA GCT A | 1 |
| anti-21-AM (backbone modified) | T_CA A_CA TCA G_TC TG_A TA_A G_CT A | 2 |
| anti-neg-AM | GCG TAT TAT AGC CGA TTA ACG A | 3 |
| anti-neg-AM (backbone modified) | G_CG TA_T TA_T AG_C CG_A TT_A A_CG A | 4 |

* Italic and underlined letters in the above table are phosphorothioate nucleic acid (PS) and LNA (locked nucleic acid) modified nucleic acids, respectively.

Example 3: Synthesis of MSA-Conjugated miRNA-21 Inhibitor (Anti-21-MSA)

The present inventors synthesized mouse serum albumin (MSA)-conjugated miRNA-21 inhibitors. Specifically, for MSA conjugation, the present inventors reacted various molar ratio (1~20) of MSA having the thiol functional group of cysteine (cys-34) with the maleimide functional group of anti-21-MI prepared in the Example 2 in phosphate buffer saline (PBS) at 37° C. for various times (5 minutes to 4 hours). Anti-21-MSA formed by increasing the ratio of MSA in the mixing process of mouse serum albumin and anti-21-MI was obtained by 10% SDS-PAGE. The samples were analyzed by reverse-phase HPLC (Agilent Technologies 1200 series, Agilent Technologies, USA) using a C18 analytical column (H2O: Acetonitrile 10:90 to 80:20, 30 min, 230 nm). The anti-21-MSA was then purified using Amicon Ultra-0.5 mL Centrifugal Filters (MWCO 30 kDa, Merck Millipore, Darmstadt, Germany) and quantitated by BCA protein quantification assay (FIG. 1A).

Figure 1B:
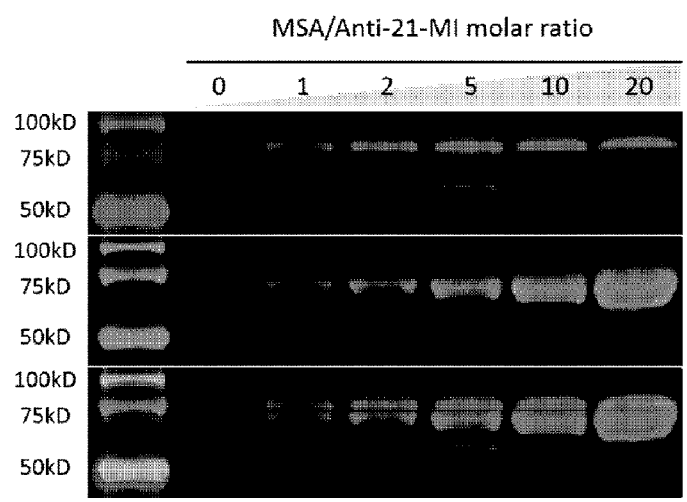
FIG. 1B is an SDS-page image showing the anti-miR-21-albumin conjugate (hereinafter referred to as "anti-21-MSA") formed while raising the albumin ratio in the mixing process of albumin and anti-miR-21 maleimide (hereinafter referred to as "anti-21-MI"). In the above image, red color represents anti-miR-21 linked with Cy5.5 fluorescent dye and green color represents protein staining using Coomassie brilliant blue.
Figure 1C:
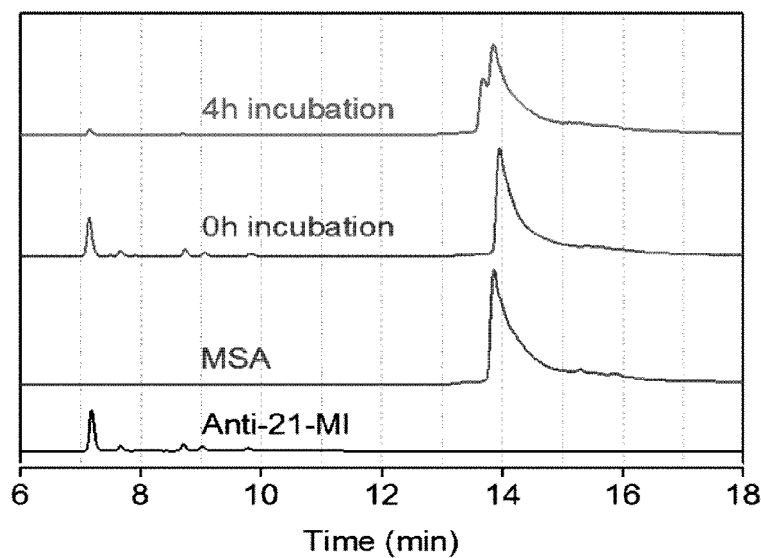
FIG. 1C is an HPLC chromatogram of samples immediately after mixing (0 hour) with anti-21-MI of the present invention and mouse serum albumin (MSA) and 4 hours after mixing.

As a result, an albumin-conjugated miRNA-21 inhibitor (anti-21-MSA) was produced by reacting with albumin (about 66 kDa) under physiological conditions and its molecular weight was about 74 kDa (FIG. 1B). The fluorescence of anti-21-MI (8 kDa) was observed at the band corresponding to 75 kDa, which means that it formed a complex (anti-21-MSA, 75 kDa) with MSA (66 kDa). Particularly, it was confirmed that anti-21-MI was saturated when reacted with about 5-fold molar ratio of MSA. Thus, in subsequent experiments, MSA was used at a molar ratio of 5-fold excess. As a result of HPLC analysis, peaks of each of anti-21-MI and MSA were identified. Although two peaks were identified immediately after mixing, anti-21-MI was decreased after 4 hours reaction and a new peak was formed at the front of the existing MSA peak. It means that anti-21-MSA was formed as a result of the reaction (FIG. 1C).

Figure 1D:
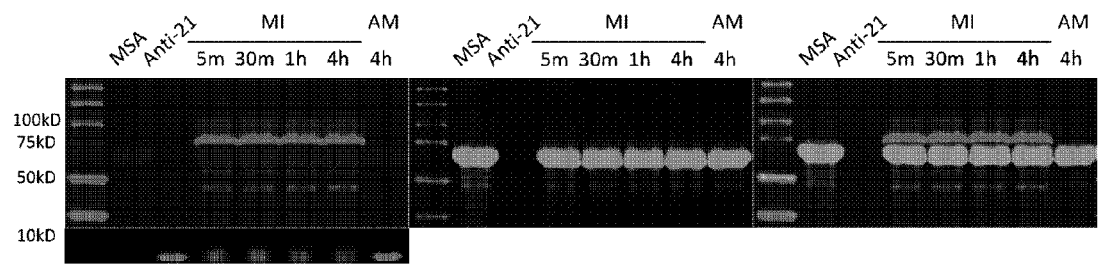
FIG. 1D is an SDS-page image obtained by analyzing anti-21-MSA produced after reacting anti-21-MI and MSA of the present invention for various times (5 minutes, 30 minutes, 1 hour and 4 hours).
Figure 1E:
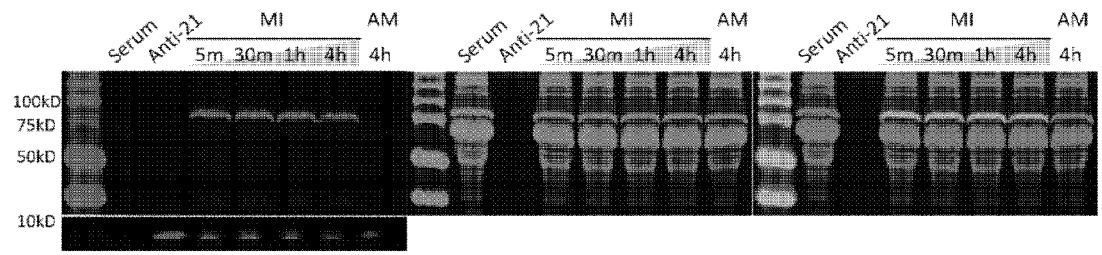
FIG. 1E shows an SDS-PAGE image obtained by analyzing anti-21-MSA produced after reacting anti-21-MI (backbone modified) of the present invention and mouse plasma for various times (5 minutes, 30 minutes, 1 hour).

In addition, anti-21-MI and anti-21-MI (backbone modified) were reacted with MSA and mouse plasma, respectively for various times (5 minutes, 30 minutes, 1 hour and 4 hours). As a result, the anti-21-MI fluorescence was observed at the peak corresponding to 75 kDa even when the anti-21-MI was reacted with mouse plasma as well as MAS. Thus, it was confirmed that the reaction of anti-21-MI and MSA occurs in the plasma of mice in which the various enzymes are present (FIG. 1D). Furthermore, the anti-21-AM showed no fluorescence at 75 kDa even after 4 hours of reaction, indicating that anti-21-AM did not react with MSA, indicating that maleimide modification is an important step in the reaction with MSA (FIG. 1E).

Example 4: Maleimide-Modified Negative Control miRNA Inhibitor (Anti-Neg-MI) Synthesis The present inventors constructed a maleimide-modified negative control miRNA inhibitor (anti-neg-MI). Specifically, except for the synthesis of the negative control miRNA inhibitor nucleic acid sequence consisting of SEQ ID NOs: 3 and 4 instead of the inhibitors of SEQ ID NOs: 1 and 2 according to the synthesis protocol using the solid support, anti-neg-AM and anti-neg-AM (backbone modified) were prepared by performing the same synthesis procedure as in Example 2.

Experimental Example 1: Analysis of Capturing Ability

The present inventors incubated the positive inhibitor (corresponding to 300 pmole of anti-21) with various molar ratio (0, 0.25, 0.5, 0.75, and 1) of miR-21 at 37° C. for 1 hour and analyzed with 8% PAGE in order to investigate ability of anti-21-MI and anti-21-MSA prepared according to an embodiment of the present invention to capture miR-21. In addition, in order to analyze capturing specificity by nucleic acid sequence, anti-21-MSA (corresponding to 300 pmole of anti-21-MI) was incubated with negative control miRNA (300 pmole) and miR-21 (300 pmole) for 1 hour at 37° C. and electrophoresis analysis was performed with 8% PAGE. In addition, incubating anti-21-MSA (corresponding to 300 pmole of anti-21-MI) with miR-21 (300 pmole) and digesting miR-21 using RNase (1 mg/ml) were repeated three times and two times, respectively, in order to analyze the possibility of recycling of albumin, one of the physiological characteristics of albumin and then capturing ability of anti-21-MSA was analyzed by electrophoresis with 8% PAGE.

Figure 2A:
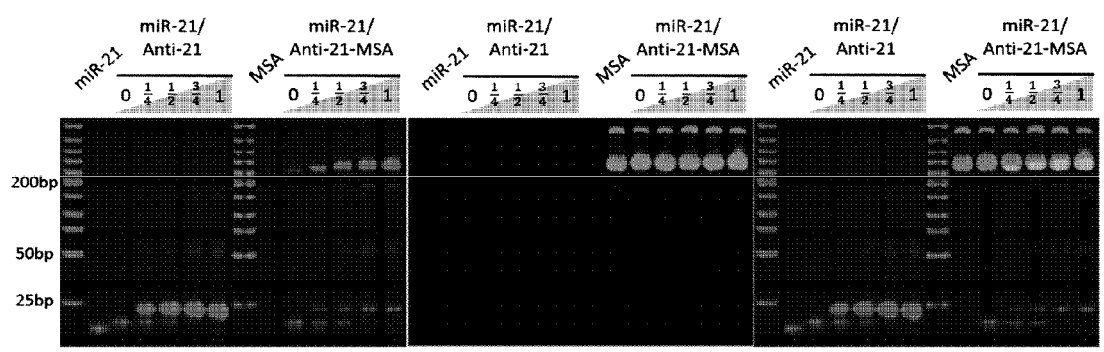
FIG. 2A is an SDS-page image of the anti-21-MI and anti-21-MSA of the present invention analyzed after incubating with various ratios (0, 0.25, 0.5, 0.75, 1) of miR-21. In the above image, red color represents nucleic acid staining with ethidium bromide (EtBr), and green color represents protein staining with Coomassie brilliant blue.
Figure 2B:
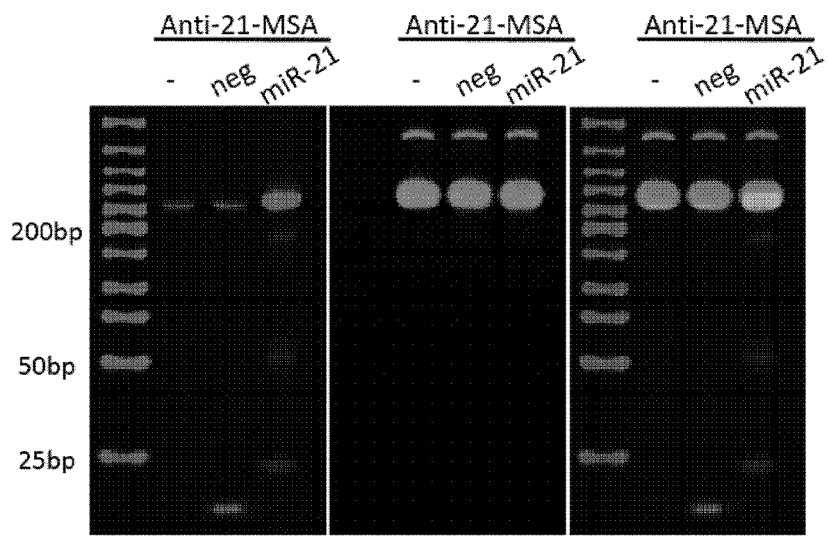
FIG. 2B is an SDS-page image of anti-21-MSA of the present invention after incubating with negative control miRNA and miR-21, respectively.
Figure 2C:
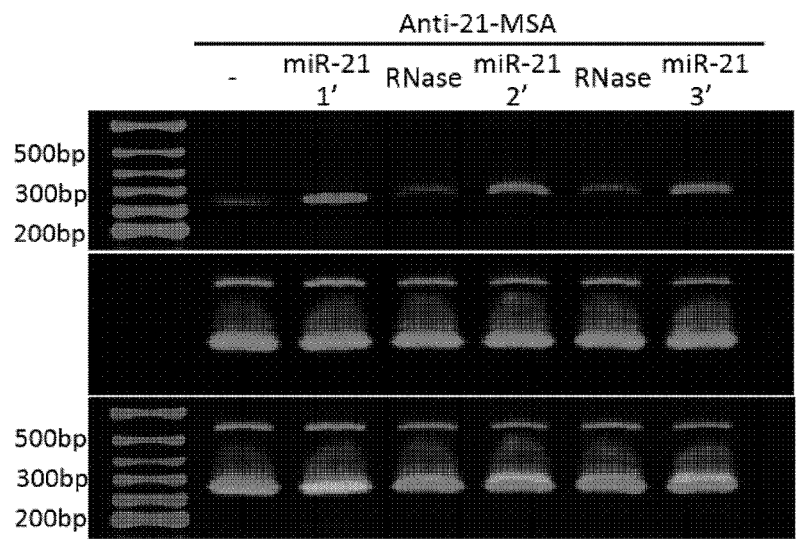
FIG. 2C is an SDS-page image showing the possibility of recycling anti-21-MSA by repeating the process of incubating anti-21-MSA of the present invention with miR-21 and then degrading miR-21 with RNase A.

As a result, it was confirmed that fluorescence intensity at the position of 22 bp corresponding to the double-stranded nucleic acid of the anti-21-MI and the position of 250 bp corresponding to the MSA of the anti-21-MSA increased and the its ability to capture miR-21 was not limited by maleimide modification and MSA conjugation, thereby (FIG. 2A). In addition, increased fluorescence of anti-21-MSA was observed only when incubated with miR-21, and it was confirmed that only the target miR-21 was captured through the specificity of the nucleic acid sequence structure (FIG. 2B). Furthermore, it was confirmed that ability of anti-21-MSA to capture miR-21 was maintained even when the incubating with miRNA-21 and digesting with RNase A were repeated three times and two times, respectively (FIG. 2C).

Experimental Example 2: Analysis of Intracellular Delivery

In order to investigate the intracellular delivery capability of the anti-21-MI and anti-21-MSA of the present invention by image analysis, U87 human-derived brain tumor cells ($1\times10^5$ cells) were seeded into a 35-mm cover-glass bottom dish and allowed to settle for 24 hours. Then the cells were treated with PBS, MSA (1.5 nmole), anti-21-MI (300 pmole), anti-21-MSA (corresponding to 300 pmole of anti-21-MI) and anti-21-MSA (corresponding to 300 pmole of anti-21-MI)+MβCD in serum-free media, respectively and incubated in a carbon dioxide incubator at 37° C. for 24 hours. Methyl-beta-cyclodextrin (MβCD) was used as an endocytosis inhibitor that inhibits albumin uptake and recycling by glycoprotein60 (gp60) in cells. After 24 hours, 4% para-formaldehyde was treated in order to fix cells and nuclear staining was performed by treating 4',6-diamidino-2-phenylindole (DAPI) solution for 10 minutes, and fluorescence from DAPI, MSA and anti-21 were observed using a confocal microscope (FV1000, Olympus, Japan). For FACS analysis, U87 cells ($1\times10^5$ cells/well) were dispensed in a 6-well plate. The cells were allowed to settle for 24 hours, and the cells were treated with PBS, MSA (1.5 nmole), anti-21-MI (300 pmole), anti-21-MSA (corresponding to 300 pmole of anti-21-MI), anti-21-MSA (corresponding to 300 pmole of anti-21-MI)+MβCD in serum-free media and cultured in a carbon dioxide incubator at 37° C. for 24 hours, respectively. Harvested cells were analyzed using Guava easyCyte Flow Cytometer (Billerica, Mass., USA).

Figure 3A:
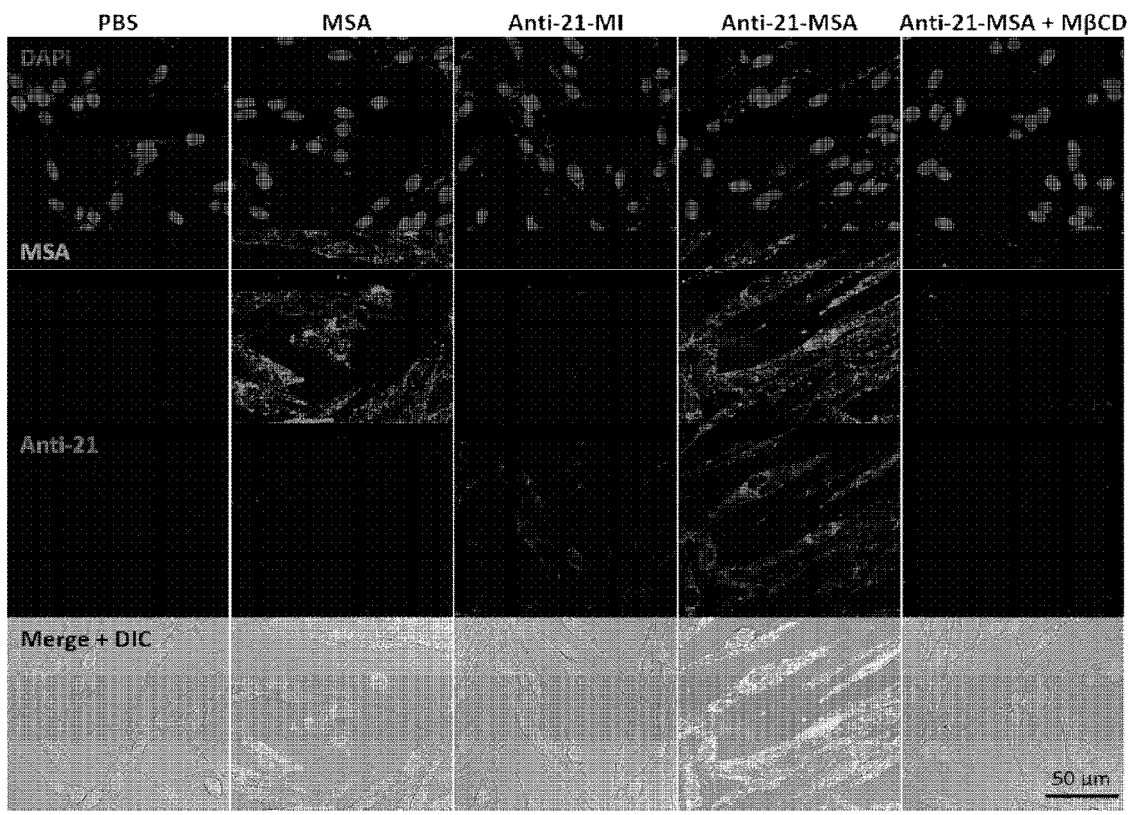
FIG. 3A is a series of confocal microscopic images of cells treated with Cy5.5 fluorescent dye-linked anti-miR-21 and/or FITC-conjugated MSA in order to analyze intracellular delivery capability of the anti-21-MSA of the present invention.

As a result, MSA was found to be superior to intracellular transport because it is a necessary factor in the metabolism of cancer cells. In addition, because anti-21-MSA shares physiological characteristics of MSA, exhibits superior intracellular delivery ability compared with anti-21-MI. Moreover, significant inhibition of intracellular delivery of MSA and anti-21 was observed in the anti-21-MSA+MβCD treated group in which MβCD capable of inhibiting albumin uptake were treated, and thus, the intracellular delivery ability of MSA associated with gp60 was found to have a significant effect on the intracellular delivery of anti-21-MI (FIG. 3A).

Figure 3B:
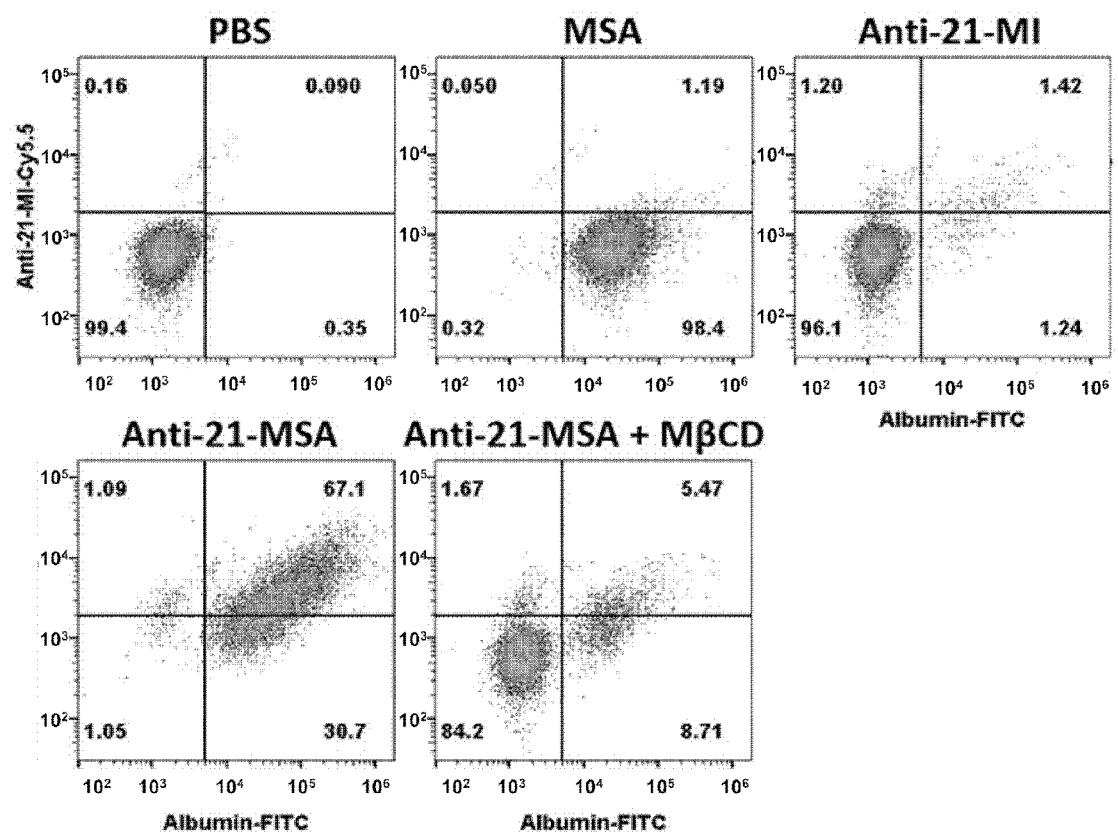
FIG. 3B is a series of FACS analysis 2-D histograms showing the intracellular delivery capability of the anti-21-MSA of the present invention.
Figure 3C:
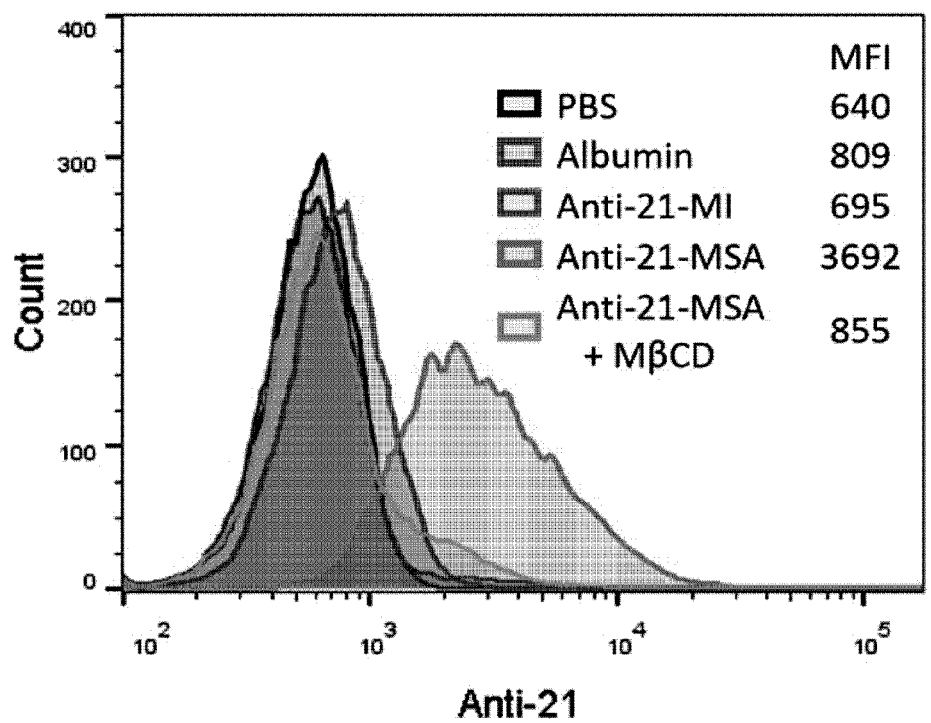
FIG. 3C is a FACS analysis histogram showing the intracellular delivery capability of albumin, anti-21-MI, anti-21-MSA of the present invention, respectively.

In addition, FACS analysis showed that MSA was delivered to 98.4% of cells in the MSA-treated group compared to the PBS-treated group. In the anti-21-MSA treated group, anti-21 were delivered to 68.1% of cells whereas delivery rate of anti-21 in the anti-21-MI treated group was 2.62%. In particular, anti-21 was transferred to 67.1% of the cells along with MSA in the anti-21-MSA group, and it was confirmed that the intracellular delivery ability of anti-21 was improved through the excellent intracellular delivery ability of MSA itself (FIG. 3B). Moreover, in the anti-21-MSA+MβCD-treated group, cells delivered with MSA decreased to 14.18%, and the number of anti-21 transferred cells decreased to 5.47%. The mean fluorescence intensity of anti-21 Cy5.5 fluorescence of the anti-21-MSA test group obtained by FACS analysis was 3692, and the mean fluorescence intensity of anti-21 CyA.5 fluorescence was 3692, which was 5.76, 4.56, 5.31, and 4.31 times for the PBS-, MSA-, anti-21-MI- and anti-21-MSA+MβCD-treated group, respectively (FIG. 3C). The above results confirmed that the intracellular delivery ability of MSA has an important effect on the intracellular delivery of anti-21-MSA.

Experimental Example 3: Anticancer Effect Analysis

The present inventors investigated the anti-cancer effect of anti-21-MI, anti-21-MSA and anti-neg-MSA of the present invention. Specifically, in order to analyze the expression of miR-21-related protein expression in vitro by miR-21 inhibitor, U87 cells ($1\times10^5$ cells/well) were dispensed in a 6-well plate and allowed to settle for 24 hours. Then MSA (1.5 nmole), anti-21-MI (300 pmole), anti-neg-MSA (corresponding to 300 pmole of anti-neg-MI) and anti-21-MSA (corresponding to 300 pmole of anti-21-MI) was treated in serum-free media and cultured in a carbon dioxide incubator at 37° C. for 48 hours, respectively. Harvested cells were lysed by using a mammalian cell lysis buffer (Sigma-Aldrich, St. Louis, Mo., USA) and proteins were purified using a centrifuge. The purified proteins were quantitated using a BCA protein quantification assay and the expression of Pdcd4, Timp3 and Mmp2 proteins associated with miR-21 was analyzed by western blot analysis using SDS-PAGE electrophoresis and the expression of the proteins was quantified through normalization using the expression level of beta-actin protein.

In addition, in order to investigate the change of cell viability by the miRNA-21 inhibitor in vitro, U87 cells ($1\times10^4$ cell/well) were dispensed into 96-well plates and allowed to settle for 24 hours. Harvested cells were washed with PBS, and treated with MSA (1.5 nmole), anti-21-MI (300 pmole), anti-neg-MSA (corresponding to 300 pmole of anti-neg-MI) and anti-21-MSA (corresponding to 300 pmole of anti-21-MI) in serum-free media and incubated in a carbon dioxide incubator at 37° C. for 24 hours, respectively. The MTT solution was then treated and the cells were incubated at 37° C. for 1 h. Formazan generated by cells metabolizing the MTT solution was dissolved in dimethyl sulfoxide (DMSO) and the cell viability was measured using the absorbance measured at a wavelength of 570 nm.

Moreover, a scratch wound recovery test was conducted to investigate the change of cell migration ability by miR-21 inhibitor in vitro. Specifically, U87 cells ($1\times10^5$ cells/well) were dispensed into a 6 well plate and allowed to settle for 24 hours. Scratch wounds were induced in the wells in which the cells were settled using a 1 ml pipette tip, and treated with PBS, MSA (1.5 nmole), anti-21-MI (300 pmole), anti-neg-MSA (corresponding to 300 pmole of anti-neg-MI) and anti-21-MSA (corresponding to 300 pmole of anti-21-MI) in serum-free media and further cultured in a serum-containing medium for 24 hours and then images were obtained using reversed phase contrast microscope (Olympus, Tokyo, Japan).

Figure 4A:
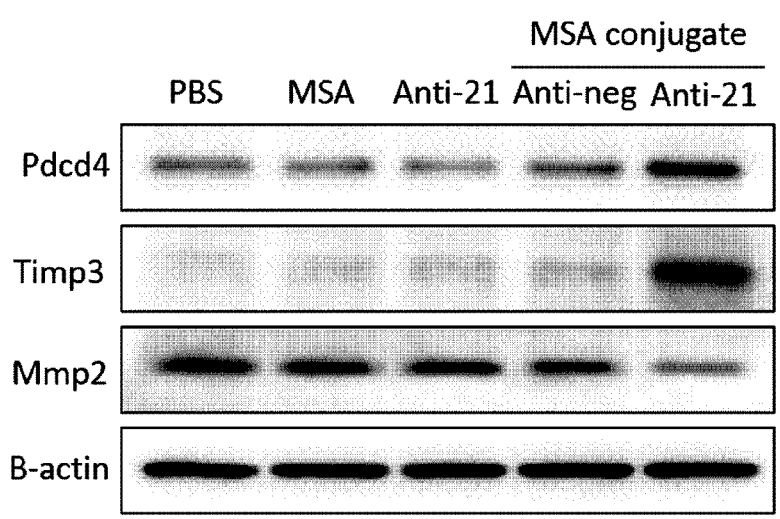
FIG. 4A is a gel image showing changes in protein expression associated with miR-21 in order to investigate anti-cancer effects of anti-21-MI, anti-21-MSA and anti-neg-MSA of the present invention.

As a result, it was shown that there was almost no change in the expression of miR-21-related proteins in the anti-21-MI-treated group with decreased intracellular delivery ability and the anti-neg-MSA test group with no ability to capture miR-21 compared to the PBS-treated control group, whereas changes of expression of miR-21-related proteins was observed in the anti-21-MSA-treated group. Particularly, the expression of Pdcd4 whose expression is inversely proportional to the expression of miR-21, Timp3, a metalloproteinase inhibiting protein increased and the expression of Mmp2, one of matrix metalloproteinase decreased (FIG. 4A). This suggests that migration of cancer cells and the expression of proteins activating angiogenesis related to cancer decreases only in the anti-21-MSA-treated group in which anti-21 was delivered to cancer cells effectively.

In addition, the anti-21-MI- and anti-21-MSA-treated groups showed significantly lower cell viability than the PBS-treated control group, confirming that the cell survival rate was reduced by the intracellularly delivered anti-21. Moreover, the anti-21-MSA-treated group showed a significantly lower cell survival rate than the anti-21-MI-treated group, and thus it was confirmed that the anti-cancer effect of anti-21 was enhanced by the enhanced intracellular delivery ability (FIG. 4B).

Figure 4B:
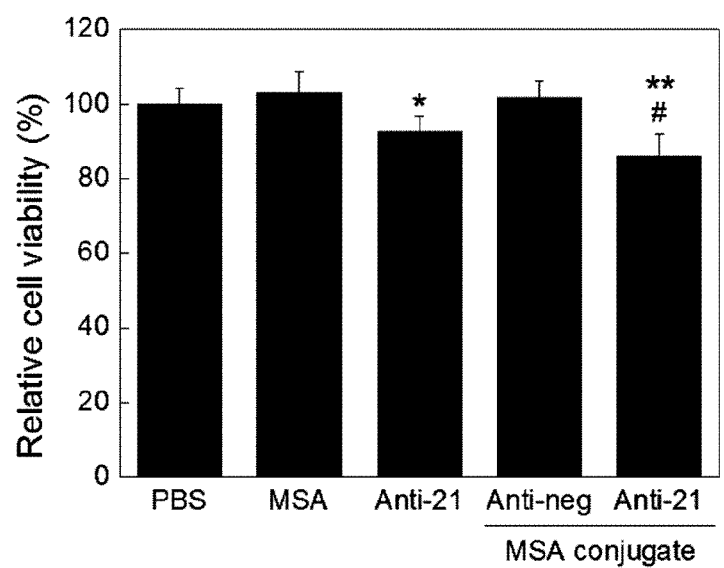
FIG. 4B is a graph showing the cell survival rate of U87 cells in order to investigate anti-cancer effect of MSA, anti-21-MI, anti-21-MSA and anti-neg-MSA of the present invention, respectively.
Figure 4C:
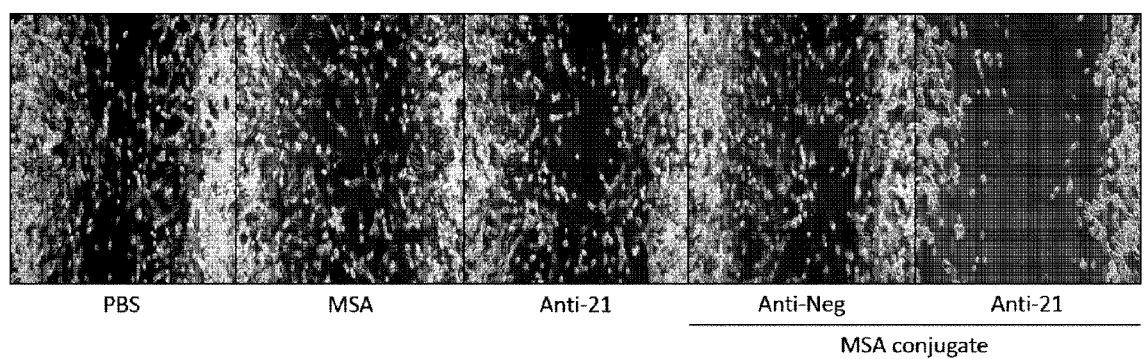
FIG. 4C is a series of images showing scratch injury recovery test results to investigate anti-cancer effects of MSA, anti-21-MI (Anti-21), anti-21-MSA and anti-neg-MSA of the present invention, respectively.
Figure 4D:
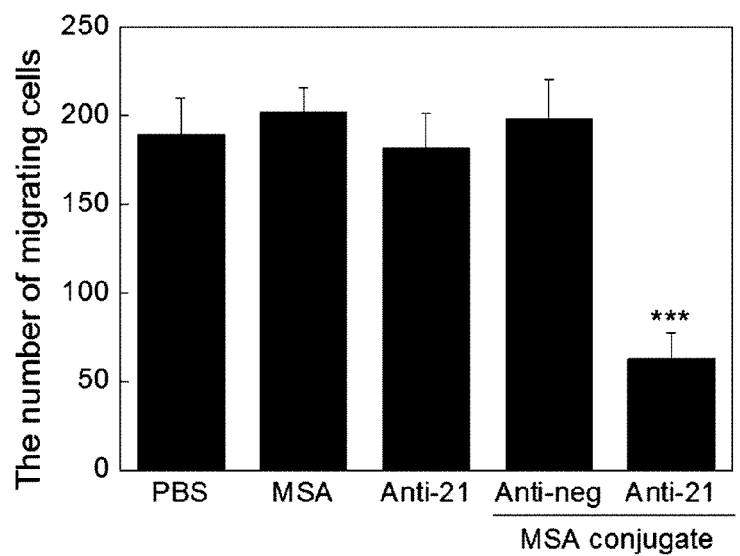
FIG. 4D is a quantitative graph analyzing the scratch injury recovery test results of FIG. 4C in order to analyze anti-cancer effects of anti-21-MI (anti-21), anti-21-MSA and anti-neg-MSA of the present invention, respectively.

In addition, the anti-21-MSA-treated cells of the scratch-wound recovery test showed that the cells did not migrate into the scratch line (red dotted line) significantly more than the other experimental groups including PBS-treated group, suggesting that the migration inhibitory effect of anti-21 increased due to enhanced intracellular delivery ability of anti-21-MSA (FIGS. 4B and 4D).

Experimental Example 4: Analysis of In Vivo Stability and Pharmacokineticsy

The present inventors analyzed stability in the plasma or in vivo stability and pharmacokinetic of anti-21-AM, anti-21-MI and anti-21-MSA of the present invention, respectively. Animal experiments in the present invention were conducted in accordance with the guidelines of Korea Institute of Science and Technology (KIST) and were approved by institutional committees. Specifically, anti-21-AM (1 nmole), anti-21-MI (1 nmole) and anti-21-MSA (corresponding to 1 nmole of anti-21-MI) were added in the plasma (50 µl) and the plasma was incubated for various times (5 min, 30 min, 1 hr, 2 hr, 4 hr, 8 hr, 12 hr, and 24 hr), respectively. The incubated samples were separated by electrophoresis on a 10% SDS-PAGE, and stability in the plasma was determined by the fluorescence intensity of each time. In addition, in order to analyze in vivo stability of anti-21-MI and anti-21-MSA and pharmacokinetic (PK), ICR mice (Nara Biotech, Inc., Republic of Korea) were injected with anti-21-AM (4 nmole), anti-21-AM (4 nmole) and anti-21-MSA (corresponding to 4 nmole of anti-21-MI) through the tail vein. Then blood was collected at the tail end of the mice at various time (15 minutes, 30 minutes, 1 hour, 3 hours, 6 hours, 9 hours, 12 hours, 24 hours, 48 hours) after the injection and the amount of anti-21 was quantified through Cy5.5 fluorescence intensity. In particular, the plasma at 48 hours from the injection was quantitated by measuring the intensity of Cy5.5 fluorescence and the plasma at 1 hour after the injection was separated by 10% SDS-PAGE.

Figure 5A:
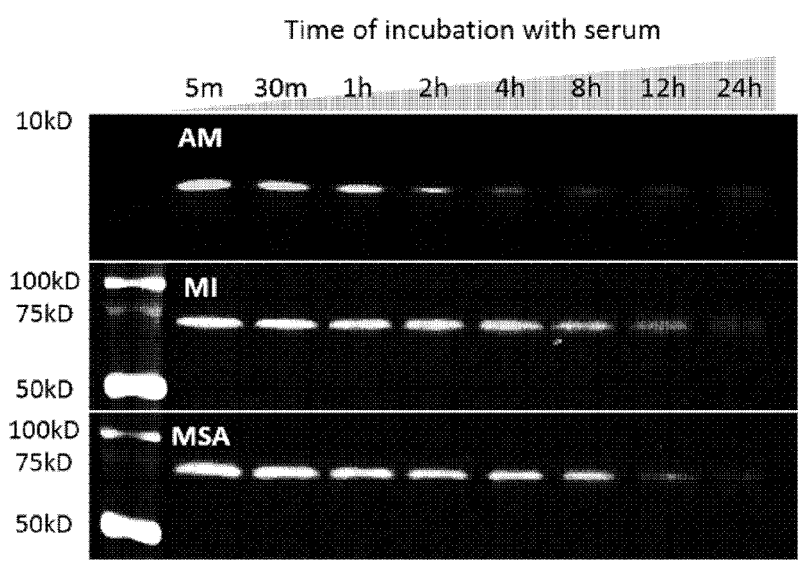
FIG. 5A is an SDS-page image analyzing stability of anti-21-AM (AM), anti-21-MI (MI) and anti-21-MSA (MSA) of the present invention in the plasma.
Figure 5B:
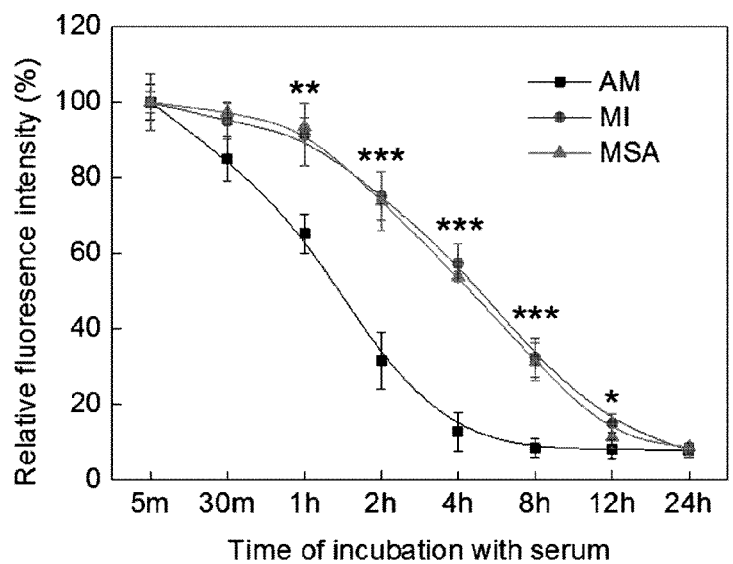
FIG. 5B is a quantitative graph analyzing stability of anti-21-AM (AM), anti-21-MI (MI) and anti-21-MSA (MSA) of the present invention in the plasma, respectively. All experiments were performed using anti-21 (backbone modified) with PS and LNA modification and linked to Cy5.5 fluorescent dye.
Figure 5C:
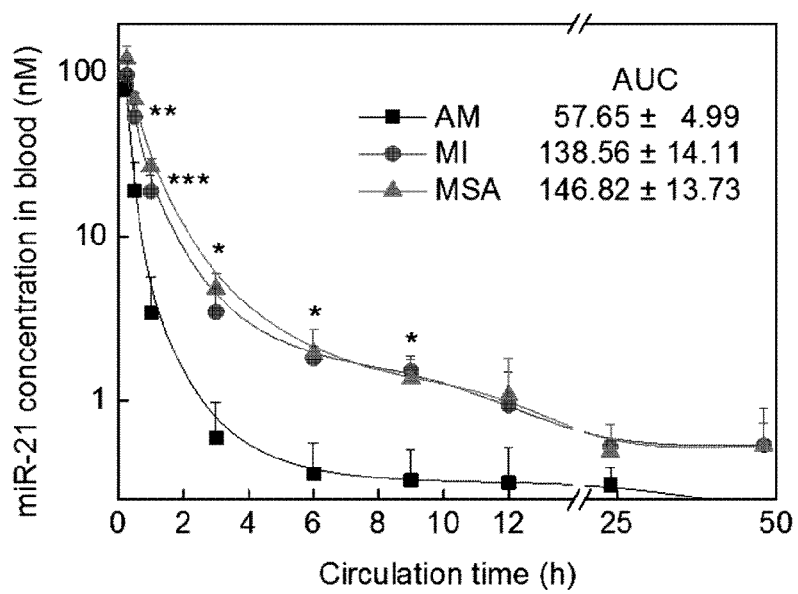
FIG. 5C is a graph showing the concentration of miR-21 in the plasma obtained after injecting anti-21-AM (AM), anti-21-MI (MI) and anti-21-MSA (MSA) of the present invention, respectively.
Figure 5D:
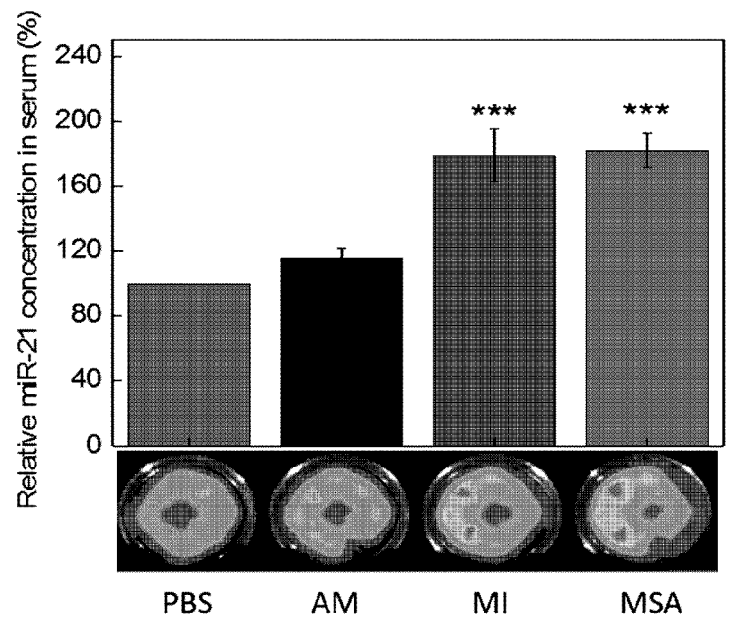
FIG. 5D is a graph showing the intensity of Cy5.5 fluorescence from plasma obtained after injecting anti-21-AM (AM), anti-21-MI (MI) and anti-21-MSA (MSA) of the present invention, respectively.
Figure 5E:
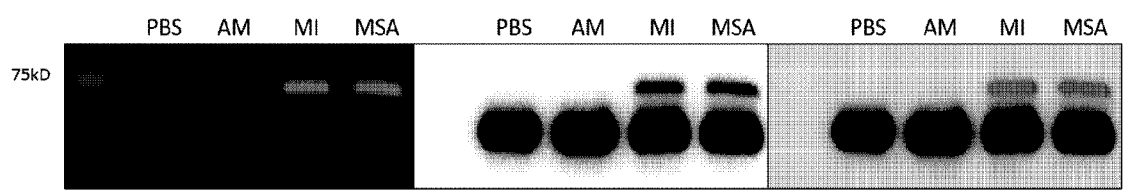
FIG. 5E is a Cy5.5 fluorescence image (left), a western blot image using anti-MSA antibodies (center) and a merged image of the two images (right) of a blot of the plasma obtained after injecting the anti-21-AM (AM), anti-21-MI (MI) and anti-21-MSA (MSA) of the present invention, respectively.

As a result, anti-21-MI reacted with MSA in the plasma and fluorescence was observed at the position corresponding to 75 kDa by quantifying fluorescence intensity, unlike anti-21-AM, which was rapidly degraded. In particular, stability in the plasma of anti-21-MI was not significantly different from that of anti-21-MSA at all time conditions, and it was confirmed that the reaction efficiency of anti-21-MI in the plasma was the same as that of anti-21-MSA which was prepared in vitro. In addition, as a result of quantitative analysis using fluorescence intensity, it was confirmed that anti-21-MI was maintained in a significant amount from 1 hour to 9 hours, unlike anti-21-AM which was rapidly degraded and cleared. In particular, similar to reactions in the plasma, anti-21-MI were not significantly different from anti-21-MSA at all time conditions, indicating that in situ reaction efficiency of anti-21-MI is same as that of anti-21-MSA prepared in vitro (FIG. 5B). Moreover, the fluorescence intensity of anti-21-MI and anti-21-MSA was significantly higher in the plasma obtained after 48 hours than that of anti-21-AM, but there is no significant difference between anti-21-MI and anti-21-MSA. These results show that the pharmacokinetic properties of anti-21-MI through in vivo reactions are the same as those of anti-21-MSA prepared in vitro (FIG. 5C). In addition, Cy5.5 fluorescence band of anti-21 corresponding to 75 kDa was observed in the plasma of anti-21-MI and anti-21-MSA-injected mice, and the fluorescence intensity quantified in the plasma was identified as the fluorescence intensity of anti-21 sharing the physiological characteristics of MSA by reacting with the MSA (FIG. 5D). Further, it was confirmed that the fluorescence of the miRNA inhibitor and the MSA chemical fluorescent band overlap in the molecular weight band of the complex (FIG. 5E).

Experimental Example 5: Analysis of In Vivo Distribution and Delivery Ability to Affected Sites The present inventors analyzed the in vivo distribution of the anti-21-AM, anti-21-MI and anti-21-MSA of the present invention and delivery ability to affected sites. In order to analyze the in vivo distribution of anti-21-AM, anti-21-MI and anti-21-MSA and to analyze delivery ability to affected site, $2 \times 10^7$ U87 Cells were injected into the left thigh (n=1) of immunodeficient nude mice to produce a tumor model. After 3 weeks, the tumor size was reached to 200-250 mm$^3$, PBS, anti-21-AM (4 nmole), anti-21-MI (4 nmole) and anti-21-MSA (corresponding to 4 nmole of anti-21-MI) were injected via the tail vein, and whole body fluorescence images were obtained using IVIS® spectrum imaging system (PerkinElmer, Waltham, Mass., USA) according to the manufacturer's instructions, at various times after the injection of the experimental materials (1 hour, 3 hours, 9 hours, 12 hours, 24 hours, and 36 hours). The fluorescence intensity of the tumor was quantified using Living Image® software (PerkinElmer, Waltham, Mass., USA). Subsequently, the main organs (liver, lung, spleen, kidney, and heart) and tumor tissues of the experimental mice were excised 36 hours after the injection of the experimental materials and fluorescence images of whole tissues were obtained using the IVIS spectrum imaging system.

Figure 6A:
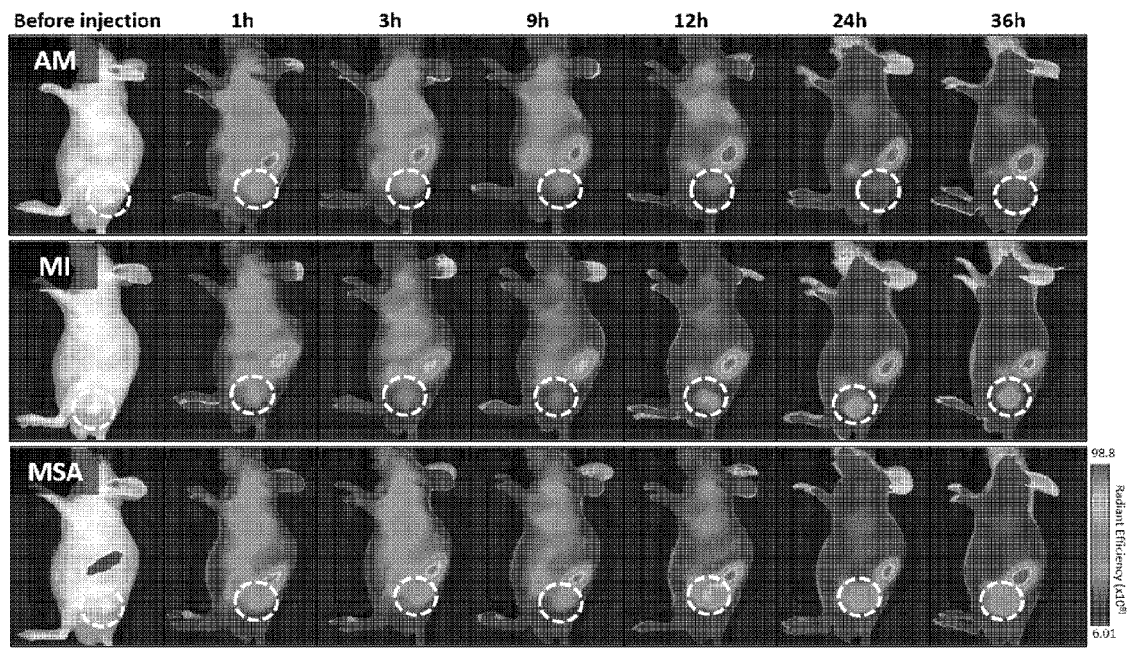
FIG. 6A is a series of whole body fluorescence images taken from mice injected with anti-21-AM (AM), anti-21-MI (MI) and anti-21-MSA (MSA) of the present invention over time, respectively in order to investigate targeting ability to affected sites.
Figure 6B:
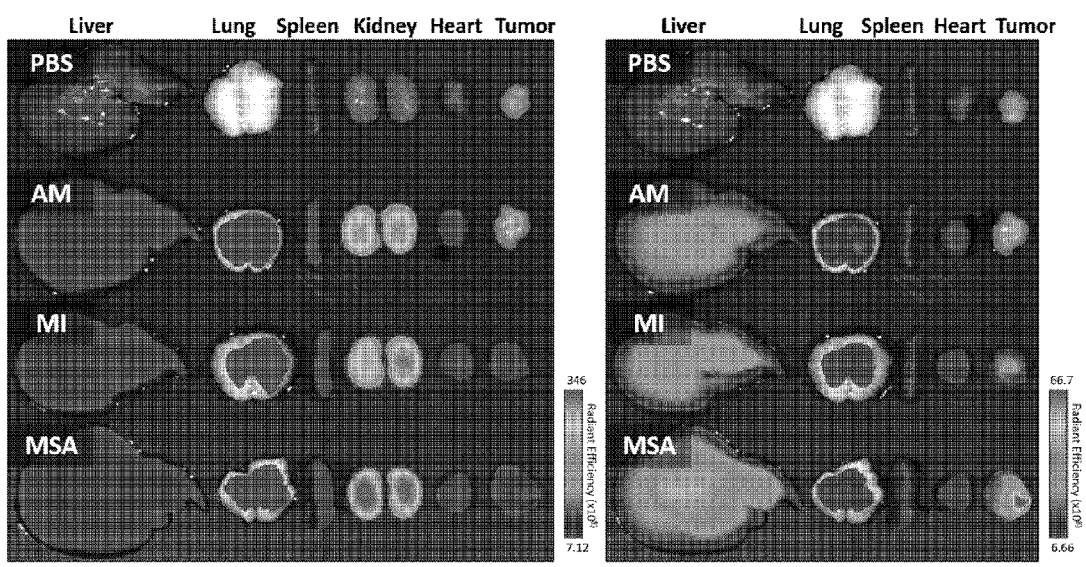
FIG. 6B is a series of fluorescence images of organs excised form the mice of FIG. 6A in order to analyze the distribution of the anti-21-AM (AM), anti-21-MI (MI) and anti-21-MSA (MSA) of the present invention and their targeting ability to disease site. The right images were obtained after removing the kidney.

As a result, the in vivo distribution of anti-21-AM was identical to that of a typical miRNA inhibitor that was rapidly degraded and cleared and accumulated in the liver and especially the kidney, while the in vivo distribution of anti-21-MI and anti-21-MSA was different from that of anti-21-AM. Particularly, at the initial time (1 hour, 3 hours, and 9 hours), fluorescence intensity in the kidney was observed to decrease. In addition, fluorescence intensity accumulated in caner tissues (white dashed circle) of anti-21-MI and anti-21-MSA increased over time, while fluorescence intensity of anti-21-AM decreased in the cancer tissues. Thus, it was confirmed that anti-21-MI and anti-21-MSA share physiological characteristics of albumin and acquire characteristics of targeting ability to cancer tissues and extended in vivo circulation time (FIG. 6A). In addition, more fluorescence was accumulated in the cancer tissues from the anti-21-MI- and anti-21-MSA-injected groups than the cancer tissues of the anti-21-AM-injected group (FIG. 6B).

Experimental Example 6: Analysis of Pharmacological Effect

The present inventors analyzed the pharmacological effects of anti-21-AM, anti-neg-MI and anti-21-MI of the present invention. Specifically, $2 \times 10^7$ U87 cells were injected into the left thigh (n=5) in immunodeficient nude mice (Nara Biotech. INC.) For the analysis of pharmacological effects, the experiment was carried out when the size of tumor reached to 50-100 mm$^3$. The experimental mice were injected with PBS, anti-21-AM (2 nmole), anti-neg-MI (2 nmole) and anti-21-MI (2 nmole) via the tail vein once every three days, respectively. After 3 days from the last injection, major organs and cancer tissues were excised and the weight of cancer tissues was measured. In order to compare the expression of miR-21-related proteins in the cancer tissues, tissue lysates were obtained from the cancer tissues using a mammalian cell lysis buffer and a Wisemix homogenizer (Daihan Scientific, Seoul, Republic of Korea) and proteins were purified using a centrifuge. The obtained proteins were quantified using BCA protein quantifying analysis. The expression of Pdcd4, Timp3, and Mmp2 related to miR-21 was compared by Western blot analysis using SDS-PAGE. Protein quantification was normalized using beta-actin protein.

Figure 7A:
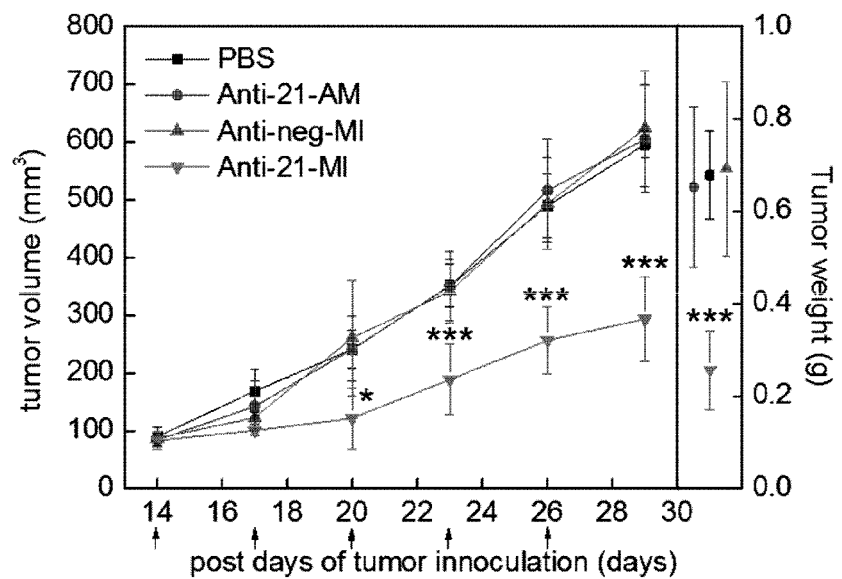
FIG. 7A is a graph showing the analysis of the weights of cancers excised from tumor model mice administered with anti-21-AM (AM), anti-21-MI (MI) and anti-21-MSA (MSA) of the present invention, respectively, in order to analyze their pharmacological effects. All experiments were performed using anti-21 (backbone modified) with PS and LNA modification.
Figure 7B:
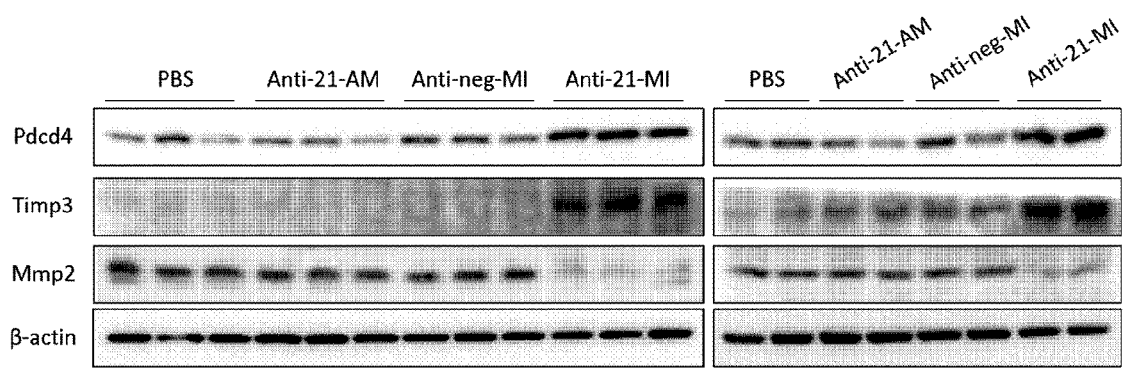
FIG. 7B is a western blot image showing changes in protein expression associated with miR-21 of cancer tissues isolated from the tumor model mice of FIG. 7A.
Figure 7C:
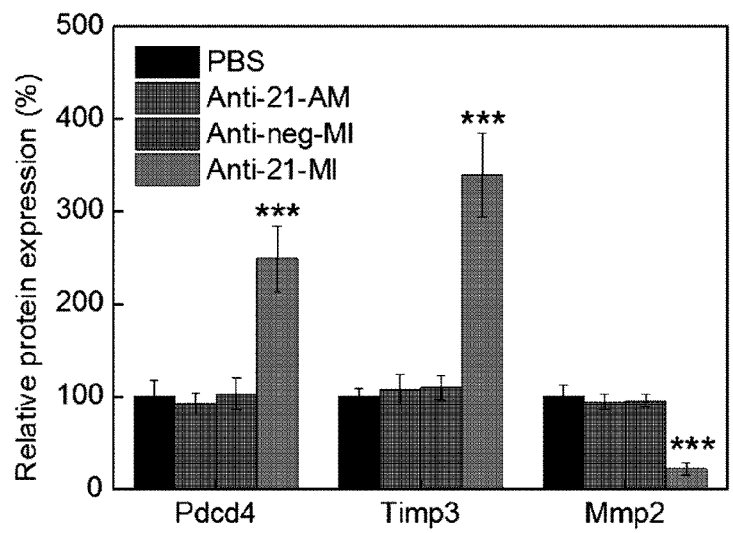
FIG. 7C is a graph showing the quantitative analysis of the expression of miR-21-related proteins in cancer tissues isolated from the tumor model mice of FIG. 7A.

As a result, anti-21-MI-injected group which reacted with MSA and captured miR-21 showed significant anti-cancer effect from 20 days after injection of tumor cells to 29 days after the injection compared with other experimental groups including the PBS-injected group. In addition, the weight of the cancer tissues at the $29^{th}$ day after the injection of cancer cells was significantly reduced in the anti-21-MI-injected group compared to other experimental groups including the PBS-injected group. The results show that, compared to anti-21-AM and anti-neg-MI, anti-21-MI shares physiological characteristics of MSA through in situ reaction and has a specific pharmacological effect on miR-21 (FIG. 7A). In addition, the expression of Pdcd4 and Timp3 was significantly increased in cancer tissues excised from anti-21-MI-injected group compared with other experimental groups including the PBS-injected group, and thus it was confirmed that only anti-21-MI-injected group in which anti-21 was effectively delivered to cancer tissues showed reduced expression of proteins activating migration of cancer cells and angiogenesis related to cancer (FIGS. 7A and 7C).

Experimental Example 7: Systemic Toxicity Analysis

The present inventors performed systemic toxicity analysis of anti-21-AM, anti-neg-MI and anti-21-MI of the present invention. Specifically, major organs were excised from the experimental animals at 3 day after the last injection of miRNA inhibitors in the analysis of pharmacological effect of the experimental example 7 and fixed with cell fixation solution. After the dehydration using ethanol and xylene, tissue blocks were prepared using paraffin and sectioned to a thickness of 6 μm using Leica Microtomes Biosystems RM2245 (Leica Camera, Wetzlar, Germany) After drying on a glass slide for 1 day, it was stained with hematoxylin and eosin (H&E).

Figure 8:
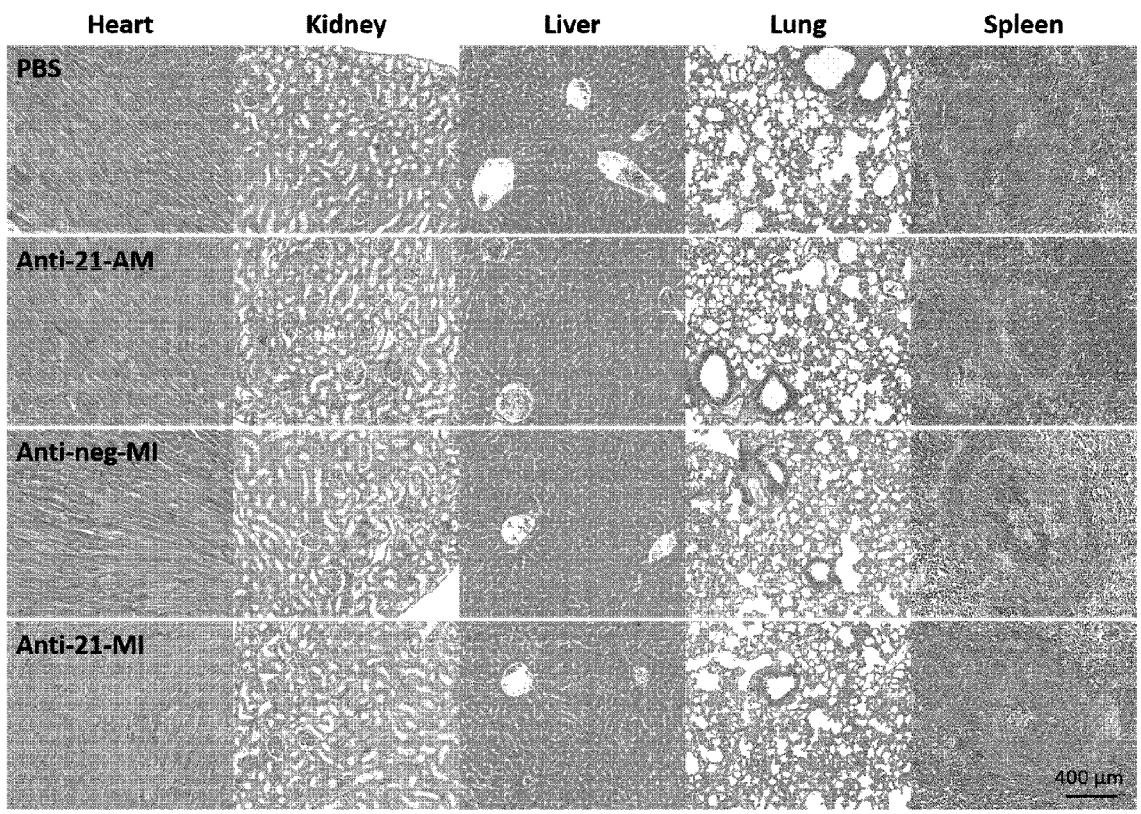
FIG. 8 is a series of a hematoxylin and eosin (H&E) staining images of sections of the major organs excised from the tumor model mice of FIG. 7A.

As a result, in the Experimental Example 5, a large amount of inhibitor accumulated in the kidney was observed. However, no significant toxicity was observed in the heart, liver, lung and spleen including the kidney. These results suggest that anti-21-MI may reduce systemic toxicity as well as exhibit anticancer effects even when administered at lower concentrations than previous conventional miRNA inhibitors (FIG. 8).

And to conclude, the anticancer agent comprising the maleimide-modified miRNA inhibitor of the present invention as an active ingredient shares the physiological properties of albumin when administered to a subject in vivo by in situ reacting with albumin, thereby may solve side effects of previous miRNA inhibitor due to low in vivo stability, rapid clearance and low targeting ability to affected sites, and thus can be used for treating various disease effectively including cancer without any additional carriers due to enhanced in vivo stability and targeting ability to affected sites.

While the present invention has been described with reference to examples and experimental examples, it is to be understood that the invention is not limited to the disclosed exemplary examples, and on skilled in the art may comprehend that there are various modifications and equivalent examples. Accordingly, the true scope of the present invention should be determined by the technical idea of the appended claims.

What is claimed is:

1. An anti-miRNA single-stranded nucleic acid maleimide derivative to which a maleimide group is added at either end of an anti-miRNA single-stranded nucleic acid molecule having a nucleic acid sequence complementary to a miRNA, wherein the miRNA is miR-21 miR-17 miR-19 or miR-155.

2. The anti-miRNA single-stranded nucleic acid maleimide derivative of claim 1, wherein the anti-miRNA single-stranded nucleic acid molecule has a partially or wholly modified backbone.

3. The anti-miRNA single-stranded nucleic acid maleimide derivative of claim 2, wherein the modified backbone has PS (phosphorothioate) modified nucleic acid, PNA (peptide nucleic acid), PMO (phosphorodiamidate morpholino oligomer) or 2'-modified nucleic acid.

4. The anti-miRNA single-stranded nucleic acid maleimide derivative of claim 3, wherein the 2'-modified nucleic acid is 2'-O-methyl (2'-O-methyl) modified nucleic acid, or a 2'-O-methoxyethyl (2'-O-MOE) modified nucleic acid.

5. The anti-miRNA single-stranded nucleic acid maleimide derivative of claim 2, wherein the modified backbone has a modification at every third nucleotide position.

6. An anti-miRNA single-stranded nucleic acid-serum albumin conjugate in which a serum albumin is covalently bound to the anti-miRNA single-stranded nucleic acid maleimide derivative of claim 1 via the maleimide group.

7. A composition for inhibiting miRNA comprising the anti-miRNA single-stranded nucleic acid molecule maleimide derivative of claim 1 as an active ingredient.

8. A composition for inhibiting miRNA comprising the anti-miRNA single-stranded nucleic acid-serum albumin conjugate of claim 6 as an active ingredient.

9. The composition of claim 7, wherein the composition is used for the treatment of a disease caused by the overexpression of the miRNA or as a reagent for studying the biological function of the miRNA.

10. The composition of claim 8, wherein the composition is used for the treatment of a disease caused by the overexpression of the miRNA or as a reagent for studying the biological function of the miRNA.

11. A composition for treating cancer comprising the anti-miRNA single-stranded nucleic acid maleimide derivative of claim 1 as an active ingredient.

12. A composition for treating cancer comprising the anti-miRNA single-stranded nucleic acid-serum albumin conjugate of claim 6 as an active ingredient.

13. A method of inhibiting a miRNA in a subject in need of comprising administering therapeutically effective amount of the anti-miRNA single-stranded nucleic acid maleimide derivative of the claim 1 to the subject.

14. A method of inhibiting a miRNA in a subject in need of, wherein the method comprise administering therapeutically effective amount of the anti-miRNA single-stranded nucleic acid-serum albumin conjugate of claim 6 to the subject.

15. A method of stabilizing an anti-miRNA single-stranded nucleic acid in a subject in need of, wherein the method comprises:
    preparing the anti-miRNA single-stranded nucleic acid maleimide derivative of claim 1; and
    administering therapeutically effective amount of the anti-miRNA single-stranded nucleic acid maleimide derivative to the subject.

16. A method of stabilizing an anti-miRNA single-stranded nucleic acid in a subject in need of, wherein the method comprises:
    preparing an anti-miRNA single-stranded nucleic acid-serum albumin conjugate in which a serum albumin is covalently bound to the anti-miRNA single-stranded nucleic acid maleimide derivative of claim 1 via the maleimide group; and
    administering therapeutically effective amount of the anti-miRNA single-stranded nucleic acid-albumin conjugate to the subject.

17. A method for treating cancer in a subject, the method comprising:

administering an anti-miR-21 single-stranded nucleic acid maleimide derivative in which a maleimide group is added to either end of an anti-miR-21 single-stranded nucleic acid having a nucleic acid sequence complementary to a miR-21 to the subject.

18. A method for treating cancer in a subject, the method comprising:

administering an anti-miR-21 single-stranded nucleic acid-albumin conjugate in which a serum albumin is covalently bound to an anti-miR-21 single-stranded nucleic acid maleimide derivative in which a maleimide group is added to either end of an anti-miR-21 single-stranded nucleic acid having a nucleic acid sequence complementary to a miR-21 via the maleimide group to the subject.

* * * * *